United States Patent

Katakami et al.

[11] Patent Number: 4,521,415
[45] Date of Patent: Jun. 4, 1985

[54] 6-(SUBSTITUTED PHENYL)-4,5-DIHYDRO-3(2H)-PYRIDAZINONE COMPOUNDS

[75] Inventors: Tsutomu Katakami; Nobuyuki Fukazawa; Hajime Iizuka, all of Kanagawa; Takashi Nishina, Chiba; Joji Kamiya, Chiba; Yasuhito Tanaka, Chiba; Takuo Nakano, Kanagawa, all of Japan

[73] Assignee: Mitsui Toatsu Kagaku Kabushiki Kaisha, Tokyo, Japan

[21] Appl. No.: 454,021

[22] Filed: Dec. 28, 1982

[30] Foreign Application Priority Data

Dec. 28, 1981 [JP] Japan .................... 56-209938

[51] Int. Cl.³ .................. C07D 237/04; A61K 31/50
[52] U.S. Cl. .................... 514/252; 544/238; 544/239; 514/247
[58] Field of Search ............ 424/250; 544/239

[56] References Cited

U.S. PATENT DOCUMENTS 3,975,388  8/1976  Hakim et al. .................. 544/239

FOREIGN PATENT DOCUMENTS 0046966  3/1982  Japan .

OTHER PUBLICATIONS

R. T. Morrison and R. N. Boyd, "Organic Chemistry", 3rd Ed., pp. 727–752, Chapters 22 and 23.

Primary Examiner—Nicholas S. Rizzo
Attorney, Agent, or Firm—Birch, Stewart, Kolasch & Birch

[57] ABSTRACT 6-(Substituted phenyl)-4,5-dihydro-3(2H)-pyridazinone compounds possessing strong platelet aggregation inhibiting activity and blood pressure depressing activity, having the general formula:

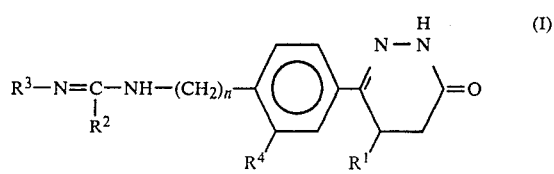

wherein $R^1$ is hydrogen or lower alkyl; $R^2$ is hydrogen, lower alkyl, lower alkylthio or the grouping $R^5$—NH— where $R^5$ is lower alkyl; $R^3$ is phenyl, pyridyl, benzyl, lower alkyl or a substituted phenyl group carrying at any desired position on the benzene ring thereof the grouping:

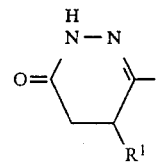

where $R^1$ has the same meaning as given above; $R^4$ is hydrogen or halogen; n is 0 or 1; and when both $R^2$ and $R^3$ are lower alkyl groups, $R^2$ and $R^3$ may be combined together with the bridging member

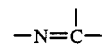

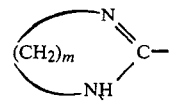

where m is 2 or 3, as well as physiologically acceptable acid-addition salts thereof, and processes for preparing them.

22 Claims, No Drawings

6-(SUBSTITUTED PHENYL)-4,5-DIHYDRO-3(2H)-PYRIDAZINONE COMPOUNDS

BACKGROUND OF THE INVENTION

1. Field of the Invention

The present invention relates to new pyridazinone derivatives possessing useful pharmacological activities and to processes for preparing the same. More particularly, the present invention relates to new 6-(substituted phenyl)-4,5-dihydro-3(2H)-pyridazinone compounds having strong platelet aggregation inhibiting activity and blood pressure depressing activity and to processes for the preparation of such new pyridazinone compounds.

2. Description of the Prior Art

Certain kinds of dihydropyridazinone derivatives are known to possess useful pharmacological activities. For example, the 6-(p-acylaminophenyl)-4,5-dihydropyridazinone-(3) compounds disclosed in Japanese Laid-Open Patent Application No. 54-9289 are reported to possess platelet aggregation inhibiting activity as well as blood pressure depressing activity. A number of studies are still being conducted to investigate useful pharmacological activities of various pyridazinone derivatives. Under such circumstances, there is a great demand in this art for developing additional new classes of pyridazinone derivatives having valuable pharmacological activities.

BRIEF SUMMARY OF THE INVENTION

Accordingly, it is an object of the present invention to provide new 6-(substituted phenyl)-4,5-dihydro-3(2H)-pyridazinone compounds.

It is another object of the present invention to provide new dihydropyridazinone derivatives possessing strong platelet aggregation inhibiting activity as well as blood pressure depressing activity.

It is still another object of the present invention to provide processes for the preparation of such new dihydropyridazinone compounds.

Other objects, features and advantages of the present invention will become apparent more fully from the following description.

DETAILED DESCRIPTION OF THE INVENTION

With a view toward preparing a new class of pyridazinone compounds having valuable pharmacological activites, the present inventors have conducted extensive research for chemically modifying 6-phenyl-4,5-dihydro-3(2H)-pyridazinone by introducing various kinds of substituents into the pyridazinone ring itself and/or the 6-phenyl group thereof. As a result of such research, it has now been found that new 6-phenyl-4,5-dihydro-3(2H)-pyridazinone compounds which have a specific substituted amidino group

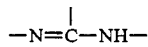

directly or indirectly bound to the 4-position of the phenyl group and which may further be substituted at the 3-position of the phenyl group and/or the 5-position of the pyridazinone group possess excellent platelet aggregation inhibiting activity and blood pressure depressing activity and are thus valuable as blood pressure depressants, antithromobolic agents and the like medicaments for the circulation system. The present invention is based on this finding.

Therefore, in accordance with the present invention, there are provided new 6-(substituted phenyl)-4,5-dihydro-3(2H)-pyridazinone compounds of the general formula:

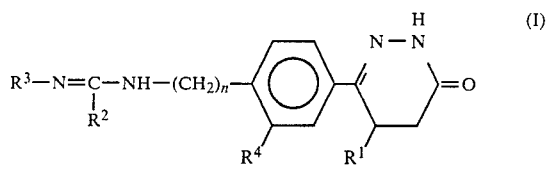

wherein $R^1$ is a hydrogen atom or a lower alkyl group; $R^2$ is a hydrogen atom, a lower alkyl group, a lower alkylthio group or the grouping $R^5$—NH— where $R^5$ is a lower alkyl group; $R^3$ is a phenyl group, a pyridyl group, a benzyl group, a lower alkyl group or a substituted phenyl group carrying at any desired position on the benzene ring thereof the grouping:

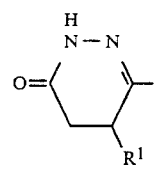

wherein $R^1$ has the same meaning as given above; $R^4$ is a hydrogen atom or a halogen atom; n is the integer 0 or 1; and when both $R^2$ and $R^3$ are lower alkyl groups, $R^2$ and $R^3$ may be combined together with the bridging member

between them to form the structure:

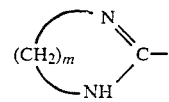

where m is the integer 2 or 3, as well as physiologically acceptable acid-addition salts thereof.

The compounds of the present invention involve the following three classes of pyridazinone compounds:

(1) 6-(substituted phenyl)-4,5-dihydro-3(2H)-pyridazinone compounds of the general formula:

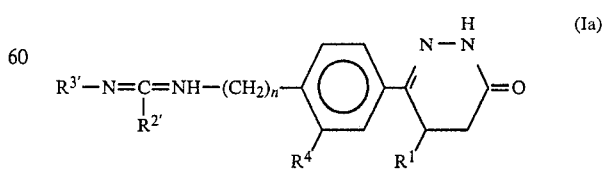

(2) 6-[4-(1,3-diazacycloalken-2-ylamino or -aminoalkyl)phenyl]-4,5-dihydro-3(2H)-pyridazinone compounds of the general formula:

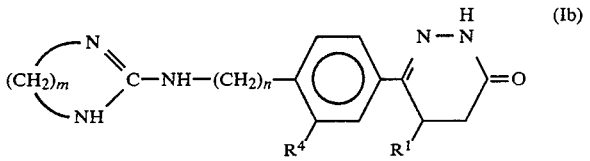 (Ib)

(3) N,N′-bis[4-(4,5-dihydro-3(2H)-pyridazinon-6-yl)-phenyl or -phenylalkyl]-acylamidine compounds of the general formula:

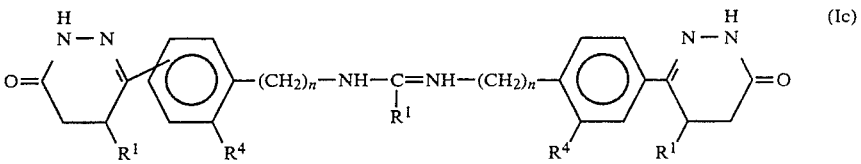 (Ic)

In these formulas, $R^{2'}$ is a hydrogen atom, a lower alkyl group, a lower alkylthio group or the grouping $R^5$—NH—, $R^{3'}$ is a phenyl group, a pyridyl group, a benzyl group or a lower alkyl group, and $R^1$, $R^4$, $R^5$, n and m have the same meanings as given above. Of the compounds represented by the general formula (Ic), preferred are those in which both 4,5-dihydro-3(2H)-pyridazinone ring exist in symmetrical positions.

In the compounds of the general formula (I), there is tautomerism in the amidine or guanidine structure and the following two tautomers exist in case of the amidine structure:

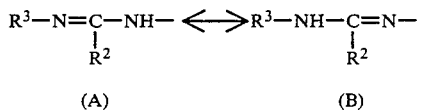

and the following three tautomers exist in case of the guanidine structure:

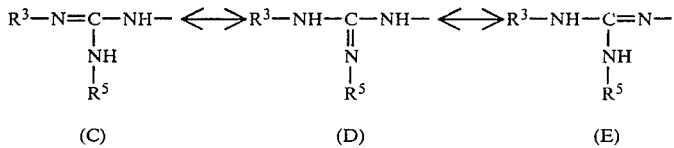

The compounds of the general formula (I) can exist as such tautomers. Accordingly, these tautomers are also involved in the end products of the present invention.

When $R^1$, $R^2$, $R^3$ and/or $R^5$ in the general formula (I) represents a lower alkyl group, this group preferably has 1 to 4 carbon atoms and may be linear or branched. Typical examples of the lower alkyl group include methyl, ethyl, n-propyl, isopropyl, n-butyl, isobutyl, sec.-butyl and tert-butyl. Thus, examples of the lower alkylamino group of the formula $R^5$—NH— include methylamino, ethylamino, n-propylamino, isopropylamino, n-butylamino, isobutylamino, sec-butylamino and tert-butylamino. Similarly, examples of $R^2$ in case of a lower alkylthio group include methylthio, ethylthio, n-propylthio, isopropylthio, n-butylthio and isobutylthio. When $R^3$ is a phenyl, pyridyl or benzyl group, this group may further be substituted on the benzene or pyridine ring by one or more lower alkyl groups having 1 to 4 carbon atoms. When $R^3$ is a pyridyl group, this group may be 2-pyridyl, 3-pyridyl or 4-pyridyl. Illustrative of $R^4$ in case of a halogen atom are fluorine, chlorine, bromine and iodine atoms.

Since the compounds of the general formula (I) carry amino nitrogen atoms in their molecules, these compounds can form acid-addition salts with various inorganic and organic acids. Mineral acids such as hydrochloric acid, hydrobromic acid, sulfuric acid and nitric acid and organic acids such as oxalic acid, succinic acid, tartaric acid and citric acid are preferable as they form physiologically acceptable acid-addition salts with the compounds of this invention. Such acid-addition salts can easily be converted into the free compounds by treating the salts with an alkaline substance such as sodium hydroxide, sodium carbonate, sodium bicarbonate or sodium acetate, potassium hydroxide, potassium carbonate or potassium bicarbonate, ammonia or a strong organic base such as methylamine or tetramethyl ammonium hydroxide, preferably in a solvent such as water or an aqueous alcohol.

Illustrative of the typical 6-(substituted phenyl)-4,5-dihydro-3(2H)-pyridazinone compounds of this invention are, for example, 6-[4-(N-benzyl-N′-methylguanidino)phenyl]-5-methyl-4,5-dihydro-3(2H)-pyridazinone,
6-[4-(N-butyl-N′-methylguanidino)phenyl]-5-methyl-4,5-dihydro-3(2H)-pyridazinone,
6-[4-(N-propyl-N′-methylguanidino)phenyl]-5-methyl-4,5-dihydro-3(2H)-pyridazinone,
6-[4-(N-ethyl-N′-methylguanidino)phenyl]-5-methyl-4,5-dihydro-3(2H)-pyridazinone,
6-[4-(N,N′-dimethylguanidino)phenyl]-5-methyl-4,5-dihydro-3(2H)-pyridazinone,
6-[4-(N-phenyl-N′-ethylguanidino)phenyl]-5-ethyl-4,5-dihydro-3(2H)-pyridazinone,
6-[4-(4-pyridyl-(2)-N′-methylguanidino)phenyl]-5-methyl-4,5-dihydro-3(2H)-pyridazinone,
6-[3-bromo-4-(1,3-diazacyclopenten-2-ylamino)-phenyl]-5-methyl-4,5-dihydro-3(2H)-pyridazinone,
6-[4-(1,3-diazacyclopenten-2-ylamino)phenyl]-5-methyl-4,5-dihydro-3(2H)-pyridazinone,
6-[4-(1,3-diazacyclopenten-2-ylamino)phenyl]-4,5-dihydro-3(2H)-pyridazinone,
6-[4-(1,3-diazacyclopenten-2-ylamino)phenyl]-5-methyl-4,5-dihydro-3(2H)-pyridazinone,
6-[4-(1,3-diazacyclohexen-2-ylamino)phenyl]-5-methyl-4,5-dihydro-3(2H)-pyridazinone,
6-[4-(N,N′-dimethylguanidinomethyl)phenyl]-5-methyl-4,5-dihydro-3(2H)-pyridazinone,
6-[4-(N-butyl-N′-methylguanidinomethyl)phenyl]-5-methyl-4,5-dihydro-3(2H)-pyridazinone, 6-[3-bromo-4-(N-propyl-N'-ethylguanidinomethyl)-
 phenyl]-5-ethyl-4,5-dihydro-3(2H)-pyridazinone,
N,N'-bis[4-(5-methyl-4,5-dihydro-3(2H)-pyridazinon-
 6-yl)phenyl]-formamidine,
N,N'-bis[2-bromo-4-(5-methyl-4,5-dihydro-3(2H)-
 pyridazinon-6-yl)phenyl]-formamidine,
N,N'-bis[4-(4,5-dihydro-3(2H)-pyridazinon-6-
 yl)phenyl]-formamidine,
N,N'-bis[4-(5-methyl-4,5-dihydro-3(2H)-pyridazinon-
 6-yl)benzyl]-formamidine,
6-[4-{N-(2-pyridyl)-formamidino}phenyl]-5-methyl-
 4,5-dihydro-3(2H)-pyridazinone,
6-[4-{N-(3-pyridyl)-formamidino}phenyl]-5-methyl-
 4,5-dihydro-3(2H)-pyridazinone,
6-[4-{N-(4-pyridyl)-formamidino}phenyl]-5-methyl-
 4,5-dihydro-3(2H)-pyridazinone, and
N,N'-bis[4-(5-methyl-4,5-dihydro-3(2H)-pyridazinon-
 6-yl)phenyl]-acetamidine,
as well as physiologically acceptable acid-addition salts thereof with various mineral acids and organic acids.

In accordance with the present invention, there is also provided a process for the preparation of the new 6-(substituted phenyl)-4,5-dihydro-3(2H)-pyridazinone compounds of the general formula (I) through several different routes.

In one embodiment of the preparation process, the compounds of the general formula (I) can be prepared by first reacting 6-(3-$R^4$-4-amino- or 3-$R^4$-4-aminoalkyl-phenyl)-4,5-dihydro-3(2H)-pyridazinone with a thioisocyanate of the formula: $R^3$—NCS in a usual manner to form a thiourea derivative of the general formula:

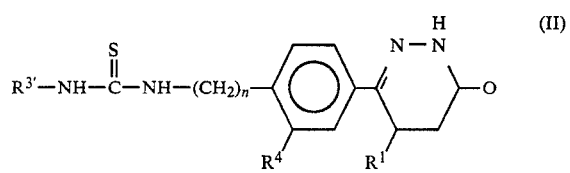

wherein $R^1$, $R^{3'}$, $R^4$ and n have the same meanings as given above, reacting this thiourea derivative with a methyl halide (usually, methyl iodide) to prepare the corresponding methylisothiuronium salt (usually, the hydroiodide) of the general formula:

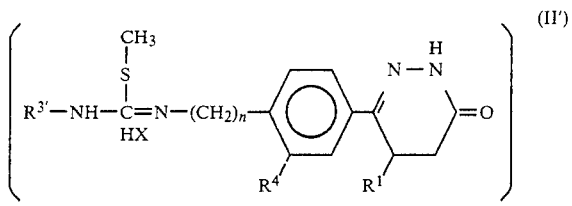

wherein X is a halogen atom and $R^1$, $R^{3'}$, $R^4$ and n have the same meanings as given above, according to a method known per se, and then reacting the methylisothiuronium salt of the formula (II') in a proper solvent with a suitable amine.

Illustrative of the solvent suitably used for the reaction are, for example, water, methanol, ethanol, propanol and dimethylformamide (referred to hereinafter simply as DMF). Examples of the amine used for this reaction include alkyl-amines such as methylamine, ethylamine, propylamine, isopropylamine and butylamine, aniline, benzylamine, 2-, 3- and 4-aminopyridines, ethylenediamine and trimethylenediamine.

In another embodiment of the process of this invention, the compounds of the general formula (I) wherein $R^2$ is a hydrogen atom or a lower alkyl group can be prepared by utilizing a general method known as a synthetic method for amidines. For example, such compounds can be prepared by reacting an imidate or an imidoyl halide of the general formula:

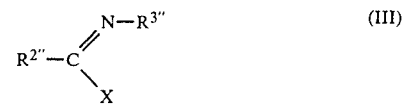

wherein $R^{2''}$ is a hydrogen atom or a lower alkyl group, $R^{3''}$ is a phenyl or pyridyl group, and X is a halogen atom, especially a chlorine atom, or a lower alkoxy group such as methoxy or ethoxy, in an appropriate solvent with a pyridazinone derivative of the general formula:

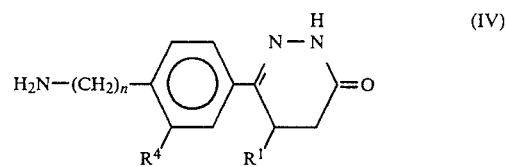

wherein $R^1$, $R^4$ and n have the same meanings as given above.

Illustrative of the solvent suitably used for this reaction are, for example, benzene, toluene ethanol and DMF.

In still another embodiment of the process of this invention, some of the compounds of the general formula (I) can be prepared by heating a compound of the general formula (IV) with a lower alkyl orthoformate or orthoacetate such as ethyl orthoformate or ethyl orthoacetate in the presence of p-toluenesulfonic acid or the like, if necessary, in a solvent such as toluene or DMF, to effect condensation while removing lower alkanols formed during the condensation reaction.

The compounds of the general formula (I) thus obtained are new chemical substances and exhibit strong platelet aggregation inhibiting activity and blood pressure depressing activity. Accordingly, the compounds of the present invention are useful as valuable medicaments for the remedy and prevention of thrombotic diseases and hypertension. Pharmaceutical formulation of the compounds of the general formula (I) and their physiologically acceptable salts can be effected by means of a non-chemical route. In order to accomplish this, the compounds and physiologically acceptable acid addition salts are brought into a suitable dosage form, together with at least one solid, liquid and/or semi-solid excipient or auxiliary, if necessary, with one or more other active ingredients.

The pharmakinetic effects of the new compounds of this invention are examined according to the following testing methods:

(1) Platelet aggregation inhibiting activity

The influence on the aggregation of platelets was examined according to the Born method [G. V. Born, Nature 194, 927 (1962)]. Blood extracted by inserting a cannula into the carotid artery of a rabbit under non-anesthetic conditions was mixed with a 3.8% solution of sodium citrate in a mixing ratio of 9:1 and the mixture was subjected to centrifugal action for 10 minutes at 1100 r.p.m., using a laboratory centrifugal separator, whereby red blood corpuscles were precipitated to yield a plasma rich in platelets (referred to hereinafter simply as PRP). A small amount of PRP was placed in a cubette of an Aglygometer and stirred with a small stirrer. To the PRP were added successively a solution of a substance to be tested (pH 7.4, physiologically isotonic) and collagen to initiate the aggregation of platelets. The difference in transmission of PRP in the process of aggregation was continuously recorded. The amount of collagen added for initiating the aggregation was set to a minimum amount, thus enabling observation of the maximum aggregation. The strength of inhibiting the aggregation by the substance to be tested was calculated from the concentration of the substance to be tested which exhibited the same inhibiting effect as shown by $10^{-4}$M aspirin. A result of this experiment is shown in Table 1 wherein the rating of the aggregation-inhibiting effect is designated by the following symbols:

| | |
|---|---|
| − | No inhibiting effect |
| ± | Weaker in the aggregation-inhibiting effect than aspirin |
| + | Equivalent in the aggregation-inhibiting effect to aspirin |
| + + | Below 10 times as much in the aggregation-inhibiting effect as aspirin |
| + + + | Below 100 times as much in the aggregation-inhibiting effect as aspirin |
| + + + + | Above 100 times as much in the aggregation-inhibiting effect as aspirin |

(2) Anti-hypertensive activity

After the development of hypertension in rats that were at least 20 weeks old, spontaneously hypertensive rats (SHR) were starved for 17 hours and used for the test. The sistolic blood pressure of the tail artery was measured by an indirect method under non-anesthetic conditions before administration of a medicament and 1, 2, 4, 6 and 24 hours after administration of the medicament. The substance to be tested was dissolved or suspended in a 0.2% CMC solution and orally administered to a group consisting of 3–5 rats showing a sistolic blood pressure of 180 mm Hg or higher. A result of the experiments is shown in Table 1.

TABLE 1

| Compounds of Example Nos. | Dosage (mg/kg) | sistolic blood pressure (mm Hg) Hours elapsed | | | | | Platelets aggregation inhibiting activity |
|---|---|---|---|---|---|---|---|
| | | 0 | 2 | 4 | 6 | 24 | |
| 1 - (c) | 4 | 190 | 190 | 183 | — | — | + + + |
| 2 | 4 | 190 | 140 | 140 | 152 | 177 | + + + |
| 7 | 4 | 183 | 183 | 183 | — | — | + + |
| 8 | 4 | 187 | 144 | 139 | 139 | 160 | ± |
| 9 | 4 | 193 | 145 | 148 | 146 | 181 | + + + |

The following examples are given merely as illustrative of the present invention and are not to be considered as limiting.

EXAMPLE 1

(a)

6-[4-(N-methylthiocarbamoylamino)phenyl]-5-methyl-4,5-dihydro-3(2H)-pyridazinone In 40 ml of dry dimethylformamide (DMF) was dissolved 8.13 g of 6-(p-aminophenyl)-5-methyl-4,5-dihydro-3(2H)-pyridazinone. To this solution was added 3.5 g of methyl thioisocyanate, and the mixture was stirred for 4 hours at room temperature. The mixture was stirred for an additional 30 minutes at 50° C. and the solvent was distilled off under reduced pressure. To the residue was added 50 ml of dichloromethane/ether (1:1) to precipitate crystals which were then collected by filtration and washed with dichloromethane, whereby 10.1 g of the above-identified compound was obtained. M.P. 213° C.

(b) Methylisothiuronium hydroiodide

In 100 ml of anhydrous methanol was dissolved 8.23 g of the product obtained in the preceding step (a). To this solution was added 5.11 g of methyl iodide, and the mixture was stirred for 2 hours at 40°–50° C. The mixture was stirred for an additional one hour under reflux. After cooling, the solvent was removed from the mixture by distillation to concentrate the mixture to 20 ml. After cooling, the precipitated crystals were collected by filtration and washed with ether whereby 12.3 g of methylisothiuronium hydroiodide was obtained. M.P. 232°–234° C. (with decomp.).

(c)

6-[4-(1,3-diazacyclopenten-2-ylamino)phenyl]-5-methyl-4,5-dihydro-3(2H)-pyridazinone A mixture of 2.09 g of the compound obtained in the foregoing step (b), 450 mg of ethylenediamine and 15 ml of ethanol was stirred for 16 hours under reflux. The solvent was distilled off and the residue was taken up in a small amount of methanol. 10 Milliliters of a 30% aqueous solution of potassium hydroxide was added to the methanolic solution and the precipitated crystals were collected by filtration, washed with water and then with a small amount of methanol, whereby 1.1 g of the above-identified compound was obtained. M.P. 270°–272° C. (with decomp.).

EXAMPLE 2

6-[4-(N-butyl-N'-methylguanidino)phenyl]-5-methyl-4,5-dihydro-3(2H)-pyridazinone hydrochloride Using the compound obtained in Example 1(b) and butylamine, the reaction was carried out in the same manner as described in Example 1(c) to obtain the above-identified compound.

EXAMPLE 3

6-[4-(N-propyl-N'-methylguanidino)phenyl]-5-methyl-4,5-dihydro-3(2H)-pyridazinone hydrochloride Using the compound obtained in Example 1(b) and propylamine, the reaction was carried out in the same manner as described above to obtain the above-identified compound.

EXAMPLE 4

6-[4-(N-benzyl-N'-methylguanidino)phenyl]-5-methyl-4,5-dihydro-3(2H)-pyridazinone hydrochloride Using the compound obtained in Example 1(b) and benzylamine, the reaction was carried out in the same manner as described in Example 2 to obtain the above-identified compound which was in the form of an amorphous powder.

EXAMPLE 5

6-[3-bromo-4-(1,3-diazacyclopenten-2-ylamino)phenyl]-5-methyl-4,5-dihydro-3(2H)-pyridazinone Using 6-(4-amino-3-bromophenyl)-5-methyl-4,5-dihydro-3(2H)-pyridazinone and methylthioisocyanate, the reaction was carried out in the same manner as described in Example 1(b) to the corresponding methylisothiuronium salt which was then reacted with ethylenediamine in the same manner as described in Example 1(c) to afford the above-identified compound. M.P. 265°–267° C. (with decomp.).

EXAMPLE 6

6-[4-(N,N'-dimethylguanidinomethyl)phenyl]-5-methyl-4,5-dihydro-3(2H)-pyridazinone (a) Reaction of 6-[4-(3-methylthioureidomethyl)-phenyl]-5-methyl-4,5-dihydro-3(2H)-pyridazinone with methyl iodide was carried out in the same manner as described in Example 1(b) to obtain the corresponding methylisothiuronium hydroiodide.

(b) In 2 ml of methanol was dissolved the methylisothiuronium hydroiodide obtained in the preceding step (a). To this solution was added 4 ml of a 40% aqueous solution of methylamine, and the mixture was stirred for 6 hours at room temperature. After removing the solvent from the mixture by distillation, 2-N hydrochloric acid was added to the residue and any insoluble matter was eliminated. To this acidic solution was added 10-N potassium hydroxide in order to make the solution strongly alkaline. The solution was then extracted with dichloromethane and the organic phase was dried. The solvent was distilled off and ether was added to the residue to effect crystallization, whereby 1.1 g of the compound identified in the heading, 6-[4-(N,N'-dimethylguanidinomethyl)phenyl]-5-methyl-4,5-dihydro-3(2H)-pyridazinone, was obtained. M.P. 190°–192° C. (with decomp.).

EXAMPLE 7

6-[4-(1,3-diazacyclopenten-2-ylaminomethyl)phenyl]-5-methyl-4,5-dihydro-3(2H)-pyridazinone Using the methylisothiuronium salt obtained in Example 6(a) and ethylenediamine, the reaction was carried out in the same manner as described in Example 1(c) to obtain the above-identified compound in the form of an amorphous powder.

EXAMPLE 8

N,N'-bis[4-(5-methyl-4,5-dihydro-3(2H)-pyridazinon-6-yl)-phenyl]-formamidine

In 20 ml of DMF was dissolved 2.03 g of 6-(p-aminophenyl)-5-methyl-4,5-dihydro-3(2H)-pyridazinone. To this solution were added 10 ml of ethyl orthoformate and a small amount of p-toluenesulfonic acid, and the mixture was heated under agitation for 2 hours in a steam bath. After cooling, the precipitated crystals were collected by filtration and recrystallized from water-DMF, whereby 1.2 g of the compound identified in the heading herein was obtained. M.P. 306°–308° C.

EXAMPLE 9

6-[4-{N-(2-pyridyl)-formamidino}phenyl]-5-methyl-4,5-dihydro-3(2H)-pyridazinone

In 15 ml of DMF was dissolved 1.52 g of 6-(p-aminophenyl)-5-methyl-4,5-dihydro-3(2H)-pyridazinone. To this solution was added 1.35 g of N-(2-pyridyl)-formiminoethyl ether prepared from 2-aminopyridine and ethyl orthoformate, and the mixture was stirred for one hour at 60° C. After cooling, the precipitated crystals were collected by filtration and washed with dichloromethane-DMF, whereby 2.1 g of the above-identified compound was obtained. M.P. 243°–245° C.

It is to be understood that the preceding representative examples may be varied within the scope of the present specification, both as to the reactants and reaction conditions, by one skilled in the art to achieve essentially the same results.

As many apparently widely different embodiments of this invention may be made without departing from the spirit and scope thereof, it is to be understood that this invention is not limited to the specific embodiments thereof except as defined in the appended claims.

What is claimed is:

1. A 6-(substituted phenyl)-4,5-dihydro-3(2H)-pyridazinone compound of the formula:

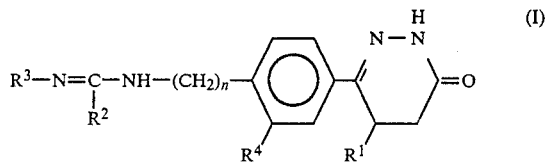

wherein $R^1$ is a lower alkyl group; $R^2$ is a hydrogen atom, a lower alkyl group, a lower alkylthio group or the grouping $R^5$—NH— where $R^5$ is a lower alkyl group; $R^3$ is a phenyl group, a pyridyl group, a benzyl group, a lower alkyl group or a substituted phenyl group carrying at any desired position on the benzene ring thereof the grouping:

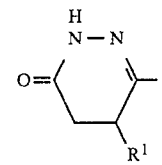

where $R^1$ has the same meaning as given above; $R^4$ is a hydrogen atom or a halogen atom; n is 0 or 1; and when both $R^2$ and $R^3$ are lower alkyl groups, $R^2$ and $R^3$ may be combined together with the bridging member

between them to form the structure:

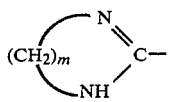

where m is 2 or 3, or a physiologically acceptable acid-addition salt thereof.

2. A compound according to claim 1, having the formula:

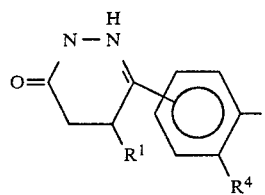

wherein $R^{2'}$ is a hydrogen atom, a lower alkyl group, a lower alkylthio group or the grouping $R^5$—NH—; $R^{3'}$ is a phenyl group, a pyridyl group, a benzyl group or a lower alkyl group; and $R^1$, $R^4$, $R^5$, and n have the same meanings as defined in claim 1, or a physiologically acceptable acid-addition salt thereof.

3. A compound according to claim 2, wherein $R^1$ is a methyl group.

4. A compound according to claim 2, wherein $R^4$ is a hydrogen atom.

5. A compound according to claim 2, wherein n is 0.

6. A compound according to claim 2, wherein $R^3$ is a pyridyl group.

7. A compound according to claim 2, wherein $R^5$ is a methyl group.

8. A 6-(substituted phenyl)-4,5-dihydro-3(2H)-pyridazinone compound according to claim 1, having the formula:

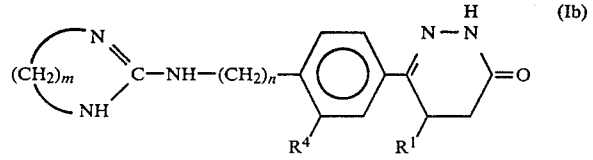

wherein $R^1$, $R^4$, n and m have the same meanings as defined in claim 1, or a physiologically acceptable acid-addition salt thereof.

9. A compound according to claim 8, wherein $R^1$ is a methyl group.

10. A compound according to claim 8, wherein $R^4$ is a hydrogen atom.

11. A compound according to claim 8, wherein n is 0.

12. A compound according to claim 8, wherein m is 2.

13. A 6-(substituted phenyl)-4,5-dihydro-3(2H)-pyridazinone compound according to claim 1, having the formula:

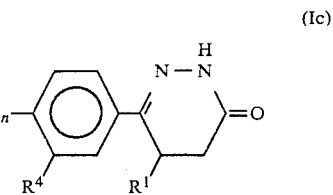

wherein $R^1$, $R^4$ and n have the same meanings as defined in claim 1, or a physiologically acceptable acid-addition salt thereof.

14. A compound according to claim 13, wherein $R^1$ is a methyl group.

15. A compound according to claim 13, wherein $R^4$ is a hydrogen atom.

16. A compound according to claim 13, wherein n is 0.

17. A pharmaceutical composition comprising an effective platelet aggregation inhibiting or blood pressure depressing amount of at least one compound according to claim 1, and a pharmaceutically acceptable excipient or auxiliary.

18. A pharmaceutical composition comprising an effective platelet aggregation inhibiting or blood pressure depressing amount of at least one compound according to claim 2, and a pharmaceutically acceptable excipient or auxiliary.

19. A pharmaceutical composition comprising an effective platelet aggregation inhibiting or blood pressure depressing amount of at least one compound according to claim 8, and a pharmaceutically acceptable excipient or auxiliary.

20. A pharmaceutical composition comprising an effective platelet aggregation inhibiting or blood pressure depressing amount of at least one compound according to claim 13, and a pharmaceutically acceptable excipient or auxiliary.

21. A pharmaceutical composition comprising an effective platelet aggregation inhibiting or blood pressure depressing amount of at least one compound according to claim 3, and a pharmaceutically acceptable excipient or auxiliary.

22. A pharmaceutical composition comprising an effective platelet aggregation inhibiting or blood pressure depressing amount of at least one compound according to claim 6, and a pharmaceutically acceptable excipient or auxiliary.

* * * * *